(12) United States Patent
Stice et al.

(10) Patent No.: US 7,291,764 B1
(45) Date of Patent: *Nov. 6, 2007

(54) CLONING PIGS USING NON-QUIESCENT DIFFERENTIATED DONOR CELLS OR NUCLEI

(75) Inventors: Steven L. Stice, Belchertown, MA (US); Jose Cibelli, Amherst, MA (US); James Robl, Belchertown, MA (US); Paul Golueke, Belchertown, MA (US)

(73) Assignee: University of Massachusetts, a Public Institution of Higher Education of the Commonwealth of Massachusetts, as Represented by its Amherst Campus, Office of Vice Chancellor for Research at Amherst, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/394,902

(22) Filed: Sep. 13, 1999
(Under 37 CFR 1.47)

Related U.S. Application Data

(63) Continuation-in-part of application No. 08/888,057, filed on Jul. 3, 1997, now Pat. No. 6,235,969, which is a continuation-in-part of application No. 08/781,752, filed on Jan. 10, 1997, now Pat. No. 5,945,577.

(51) Int. Cl.
  *C12N 15/00* (2006.01)
  *C12N 5/00* (2006.01)
  *A01K 67/00* (2006.01)
(52) U.S. Cl. .............. 800/24; 800/8; 800/17; 800/435; 800/325; 800/383
(58) Field of Classification Search ........ 435/455, 435/463, 320.1, 325, 383; 800/3, 18, 21, 800/22, 25, 8, 17, 24
See application file for complete search history.

(56) References Cited

U.S. PATENT DOCUMENTS 5,523,226 A * 6/1996 Wheeler .................. 435/240.2
5,945,377 A * 8/1999 Stice et al. ................ 800/24
6,235,969 B1 * 5/2001 Stice et al. ................ 800/24

FOREIGN PATENT DOCUMENTS

WO   99/01164 A   1/1999

OTHER PUBLICATIONS

Fehilly et.al.; Interspecific chimaerism between sheep and goat, 1984, Nature vol. 307:634-636.*
Kato et.al.; Nuclear Transplantation of Mouse Fetal Germ Cells Into Enucleated Two-Cell Embryos, 1992, Theriogenology 37:769-778.*
Fodor et.al.; Expression of a Functional human complement inhibitor in a transgeneic pig as a model for the prevention of xenogeneiic hyperacute organ rejection, 1994, Proc. Natl. Acad. Sci., vol. 91: 11153-11157.*
Strojek et. al.; A Method for Cultivating Morphologically Undifferentiated Embryonic Stem Cells From Porcine Blastocysts, 1990, Theriogenology, vol. 33, No. 4: 901-913.*
Chang et.al.; Autologous Fibroblast Implantation Feasibility and Potential Problems in Gene Replacement Therapy, 1990, Mol. Biol. Med. 7:461-470.*
Renard et al. Theriogenology, 57:203-222 (2002).*
Campbell et al. Cloning & Stem Cells, 3 :201-208 (2001).*

* cited by examiner

*Primary Examiner*—Deborah Crouch
(74) *Attorney, Agent, or Firm*—Finnegan, Henderson, Farabow, Garrett & Dunner, LLP

(57) ABSTRACT

An improved method of nuclear transfer involving the transplantation of donor differentiated pig cell nuclei into enucleated pig oocytes is provided. The resultant nuclear transfer units are useful for multiplication of genotypes and transgenic genotypes by the production of fetuses and offspring. Production of genetically engineered or transgenic pig embryos, fetuses and offspring is facilitated by the present method since the differentiated cell source of the donor nuclei can be genetically modified and clonally propagated.

6 Claims, No Drawings

CLONING PIGS USING NON-QUIESCENT DIFFERENTIATED DONOR CELLS OR NUCLEI

CROSS-REFERENCE TO RELATED APPLICATIONS

This application is a continuation-in-part of U.S. application Ser. No. 08/888,057, filed Jul. 3, 1997, now U.S. Pat. No. 6,235,969, which is a continuation-in-part of U.S. application Ser. No. 08/781,752, filed Jan. 10, 1997, now U.S. Pat. No. 5,945,577, the contents of which are hereby incorporated by reference.

FIELD OF THE INVENTION

The present invention relates to cloning procedures in which cell nuclei derived from differentiated pig cells are transplanted into enucleated porcine oocytes or blastomeres. The nuclei are reprogrammed to direct the development of cloned embryos, which can then be transferred into recipient females to produce fetuses and offspring, or used to produce pluripotent cultured inner cell mass cells (CICM). The cloned embryos can also be combined with fertilized embryos to produce chimeric embryos, fetuses and/or offspring.

BACKGROUND OF THE INVENTION

The use of ungulate inner cell mass (ICM) cells for nuclear transplantation has also been reported. For example, Collas et al., *Mol. Reprod. Dev.*, 38:264-267 (1994) discloses nuclear transplantation of bovine ICMs by microinjection of the lysed donor cells into enucleated mature oocytes. Collas et al. disclosed culturing of embryos in vitro for seven days to produce fifteen blastocysts which, upon transferral into bovine recipients, resulted in four pregnancies and two births. Also, Keefer et al., *Biol. Reprod.*, 50:935-939 (1994), disclosed the use of bovine ICM cells as donor nuclei in nuclear transfer procedures, to produce blastocysts which, upon transplantation into bovine recipients, resulted in several live offspring. Further, Sims et al., *Proc. Natl. Acad. Sci., USA*, 90:6143-6147 (1993), disclosed the production of calves by transfer of nuclei from short-term in vitro cultured bovine ICM cells into enucleated mature oocytes.

The production of live lambs following nuclear transfer of cultured embryonic disc cells has also been reported (Campbell et al., *Nature*, 380:64-68 (1996)). Still further, the use of bovine pluripotent embryonic cells in nuclear transfer and the production of chimeric fetuses has been reported (Stice et al., *Biol. Reprod.*, 54:100-110 (1996); Collas et al., *Mol. Reprod. Dev.*, 38:264-267 (1994)). Collas et al. demonstrated that granulosa cells (adult cells) could be used in a bovine cloning procedure to produce embryos. However, there was no demonstration of development past early embryonic stages (blastocyst stage). Also, granulosa cells are not easily cultured and are only obtainable from females. Collas et al. did not attempt to propagate the granulosa cells in culture or try to genetically modify those cells. Wilmut et al. (*Nature*, 365:810-813 (1997)) produced nuclear transfer sheep offspring derived from fetal fibroblast cells, and one offspring from a cell derived from an adult sheep.

Cloning pig cells is more difficult in comparison with cells of other species. This phenomenon is illustrated by the following table:

| SPECIES (from hardest to easiest to clone) | CELL TYPE CLONED | OFFSPRING PRODUCED |
|---|---|---|
| Pig (Prather, 1989) | 2 and 4 cell stage embryo | yes |
| Pig (Prather, 1989; Liu et al., 1995) | greater than 4 cell stage | no |
| Mouse (Cheong et al., 1993) | 2, 4 and 8 cell stage embryo | yes |
| Mouse (Tsunoda et al., 1993) | greater than 8 cell stage | no |
| Cattle (Keefer et al., 1994) | 64 to 128 cell stage (ICM) | yes |
| Cattle (Stice et al., 1996) | embryonic cell line from ICM | no |
| Sheep (Smith et al., 1989) | 64 to 128 cell stage (ICM) | yes |
| Sheep (Campbell et al., 1996) | embryonic cell line from ICM | yes |
| Sheep (Wilmut et al., 1997) | fetal and adult cells | yes |

There also exist problems in the area of producing transgenic pigs. By current methods, heterologous DNA is introduced into either early embryos or embryonic cell lines that differentiate into various cell types in the fetus and eventually develop into a transgenic animal. However, many early embryos are required to produce one transgenic animal and, thus, this procedure is very inefficient. Also, there is no simple and efficient method of selecting for a transgenic embryo before going through the time and expense of putting the embryos into surrogate females. In addition, gene targeting techniques cannot be easily accomplished with early embryo transgenic procedures.

Embryonic stem cells in mice have enabled researchers to select for transgenic cells and perform gene targeting. This allows more genetic engineering than is possible with other transgenic techniques. However, embryonic stem cell lines and other embryonic cell lines must be maintained in an undifferentiated state that requires feeder layers and/or the addition of cytokines to media. Even if these precautions are followed, these cells often undergo spontaneous differentiation and cannot be used to produce transgenic offspring by currently available methods. Also, some embryonic cell lines have to be propagated in a way that is not conducive to gene targeting procedures.

Methods for deriving embryonic stem (ES) cell lines in vitro from early preimplantation mouse embryos are well known. (See, e.g., Evans et al., *Nature*, 29:154-156 (1981); Martin, *Proc. Natl. Acad. Sci., USA*, 78:7634-7638 (1981)). ES cells can be passaged in an undifferentiated state, provided that a feeder layer of fibroblast cells (Evans et al., Id.) or a differentiation inhibiting source (Smith et al., *Dev. Biol.*, 121:1-9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature*, 309:255-256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod.*, 40:1027-1035 (1989); and Keefer et al., *Biol. Reprod.*, 50:935-939 (1994)). This is in contrast to nuclei from mouse embryos which beyond the eight-cell stage after transfer reportedly do not support the development of enucleated oocytes (Cheong et al., *Biol. Reprod.*, 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.*, 43:255-260 (1991), reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni et al., *J. Reprod. Fert. Suppl.*, 41:51-56 (1990) discloses maintenance and differentiation in culture of putative pluripotential embryonic cell lines from pig blastocysts. Gerfen et al., *Anim. Biotech*, 6(1):1-14 (1995) discloses the isolation of embryonic cell lines from porcine blastocysts. These cells are stably maintained in mouse embryonic fibroblast feeder layers without the use of conditioned medium, and reportedly differentiate into several different cell types during culture.

Further, Saito et al., *Roux's Arch. Dev. Biol.*, 201:134-141 (1992) reports cultured, bovine embryonic stem cell-like cell lines which survived three passages, but were lost after the fourth passage. Handyside et al., *Roux's Arch. Dev. Biol.*, 196:185-190 (1987) discloses culturing of immunosurgically isolated inner cell masses of sheep embryos under conditions which allow for the isolation of mouse ES cell lines derived from mouse ICMs. Handyside et al. reports that under such conditions, the sheep ICMs attach, spread, and develop areas of both ES cell-like and endoderm-like cells, but that after prolonged culture only endoderm-like cells are evident.

Recently, Cherny et al., *Theriogenology*, 41:175 (1994) reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell et al., *Nature*, 380:64-68 (1996) reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers et al., *Mol. Reprod. Dev.*, 40:444-454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al. reported, however, that their cell lines resembled epithelial cells more than pluripotent ICM cells.

Smith et al., WO 94/24274, published Oct. 27, 1994, Evans et al., WO 90/03432, published Apr. 5, 1990, and Wheeler et al., WO 94/26889, published Nov. 24, 1994, report the isolation, selection and propagation of animal stem cells which purportedly may be used to obtain transgenic animals. Evans et al. also reported the derivation of purportedly pluripotent embryonic stem cells from porcine and bovine species which assertedly are useful for the production of transgenic animals. Further, Wheeler et al., WO 94/26884, published Nov. 24, 1994, disclosed purported embryonic stem cells which are assertedly useful for the manufacture of chimeric and transgenic ungulates.

Thus, based on the foregoing, it is evident that many groups have attempted to produce ES cell lines, e.g., because of their potential application in the production of cloned or transgenic embryos and in nuclear transplantation.

Therefore, notwithstanding what has previously been reported in the literature, there exists a need for improved methods of cloning pigs using cultured differentiated cells as donor nuclei.

OBJECTS AND SUMMARY OF THE INVENTION

It is an object of the invention to provide novel and improved methods for producing cloned pigs by nuclear transfer using differentiated cells or nuclei derived therefrom as the donor cell or nucleus. Preferably, such differentiated cells will comprise actively dividing, i.e., non-quiescent (proliferating) cells, in $G_1$, $G_2$ or M cell phase, which optionally may be genetically modified.

It is a more specific object of the invention to provide a novel method for cloning pigs which involves transplantation of a differentiated pig cell or nucleus thereof into an enucleated pig oocyte or blastomere.

It is another object of the invention to provide a method for multiplying adult pigs having proven genetic superiority or other desirable traits.

It is another object of the invention to provide an improved method for producing genetically engineered or transgenic pigs (i.e., NT units, fetuses, offspring). The invention also provides genetically engineered or transgenic pigs, including those made by such a method.

It is a more specific object of the invention to provide a method for producing genetically engineered or transgenic pigs by which a desired DNA sequence is inserted, removed or modified in a differentiated pig cell or cell nucleus prior to use of that differentiated cell or cell nucleus for formation of a NT unit. The invention also provides genetically engineered or transgenic pigs made by such a method.

It is another object of the invention to provide a novel method for producing pig CICM cells which involves transplantation of a nucleus of a differentiated pig cell or such differentiated pig cell into an enucleated pig oocyte or blastomere, and then using the resulting NT unit to produce pluripotent CICM cells. The invention also provides pluripotent pig CICM cells and cell lines produced by such a method.

It is another object of the invention to use such pig CICM cells for therapy or diagnosis.

It is a specific object of the invention to use such pig CICM cells for treatment or diagnosis of any disease wherein cell, tissue or organ transplantation is therapeutically or diagnostically beneficial. The CICM cells may be used within the same species or across species, e.g., for human therapy.

It is another object of the invention to use cells or tissues derived from pig NT units, fetuses or offspring for treatment or diagnosis of any disease wherein cell, tissue or organ transplantation is therapeutically or diagnostically beneficial. Such diseases and injuries include Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases. The tissues may be used within the same species or across species.

It is another specific object of the invention to use cells or tissues derived from pig NT units, fetuses or offspring, or pig CICM cells produced according to the invention for the production of differentiated cells, tissues or organs.

It is another specific object of the invention to use cells or tissues derived from pig NT units, fetuses or offspring, or pig CICM cells produced according to the invention in vitro, e.g. for study of cell differentiation and for assay purposes, e.g. for drug studies. For example, pig CICMs can be introduced into SCID mice.

It is another object of the invention to use cells, tissues or organs produced from such tissues derived from pig NT units, fetuses or offspring, or pig CICM cells to provide improved methods of transplantation therapy. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to provide genetically engineered or transgenic tissues derived from pig NT units, fetuses or offspring, or pig CICM cells produced by inserting, removing or modifying a desired DNA sequence in a differentiated pig cell or cell nucleus prior to use of that differentiated cell or cell nucleus for formation of a NT unit.

It is another object of the invention to use the transgenic or genetically engineered tissues derived from pig NT units, fetuses or offspring, or pig CICM cells produced according to the invention for gene therapy, in particular for the treatment and/or prevention of the diseases and injuries identified, supra.

It is another object of the invention to use the tissues derived from pig NT units, fetuses or offspring, or pig CICM cells produced according to the invention, or transgenic or genetically engineered tissues derived from pig NT units, fetuses or offspring, or pig CICM cells produced according to the invention as nuclear donors for nuclear transplantation.

It is another object of the invention to use transgenic or genetically engineered pig offspring produced according to the invention in order to produce pharmacologically important proteins.

Thus, in one aspect, the present invention provides a method for cloning a pig (e.g., embryos, fetuses, offspring). The method comprises:

(i) inserting a desired differentiated pig cell or cell nucleus into a pig oocyte, or blastomere, which is optionally enucleated under conditions suitable for the formation of a nuclear transfer (NT) unit;

(ii) removing the endogenous nucleus from said pig oocyte or blastomere if recipient pig oocyte or blastomere was not previously enucleated;

(iii) activating the resultant nuclear transfer unit; and (iv) transferring said cultured NT unit to a host pig such that the NT unit develops into a fetus.

Optionally, the activated nuclear transfer unit is cultured until greater than the 2-cell developmental stage. The culture medium will comprise known substituents, e.g., hormones, salts, that promote NT embryo development and may further optionally be cultured in the presence of compounds that inhibit apoptosis, e.g., caspase inhibitors. However, this is not required as one cell NT embryos can be transferred with resultant fetal development virtually immediately after NT activation.

Further, the host pig will optionally comprise "helper embryos", e.g., normal pig embryos, parthenogenetic embryos or tetraploid embryos to facilitate development of cloned embryo. The number of helper embryos will preferably number from two to one about one hundred, preferably two to fifty, more preferably two to ten embryos.

The cells, tissues and/or organs of the fetus are advantageously used in the area of cell, tissue and/or organ transplantation, or production of desirable genotypes.

The present invention also includes a method of cloning a genetically engineered or transgenic pig, by which a desired DNA sequence is inserted, removed or modified in the differentiated pig cell or cell nucleus prior to insertion of the differentiated pig cell or cell nucleus into the optionally enucleated oocyte or blastomere. Genetically engineered or transgenic pigs produced by such a method are advantageously used in the area of cell, tissue and/or organ transplantation, production of desirable genotypes, and production of pharmaceutical proteins.

If the cloned fetus, embryo, or offspring is to be used to produce cells, tissues or organs for transplantation, it is also desirable to introduce one or more genetic modifications to inhibit the risk of rejection. For example, it is known that specific carbohydrate epitopes are involved in rejection responses, i.e., Gal$\alpha$1-Gal on the vascular endothelium. Therefore, it may be advantageous to knock out genes that encode these epitopes or replace such epitopes (e.g., mask) with other carbohydrate epitopes ("competitive glycosylation") that are present in human proteins. In particular, introduction of the gene for the human histo-blood O(H) antigen, for which 90% of humans do not elicit antibodies against, in order to delete 90% of $\alpha$Gal expression is one option. Alternatively, the $\alpha$Gal epitopes may be removed enzymatically in vivo by introducing the cDNA for $\alpha$galactosidase, preferably expressed under the control of a strong regulatable or constitutive promoter. Still another option is to eliminate expression of the galactosyl transferase enzyme, e.g., by homologous recombination. Also, as this will introduce new carbohydrate epitopes, it may be desirable to eliminate these epitopes also by knockout, or enzymatically.

Also, because it is known that major histo-compatibility complex (MHC) class I antigens elicit an immune response, it may be desirable to eliminate expression of genes involved in such expression, e.g., beta 2-microglobulin (a peptide that forms part of the class I molecule which is necessary for assembly and expression), the proteasomal subunits LMP-2 and LMP-7, and/or the peptide transporters TAP-1 and/or TAP-2 (TAP-1 and TAP-2 transport the peptide fragments across the membrane of the endoplasmic reticulum at the start of their journey to the cell surface.)

Still further, supra-physiologic down-regulation of local expression in the donor tissues of inhibitory cytokines, such as IL-4, soluble CTLA-4, CTLA4-Ig, anti-CD40, anti-CD40-L (CD154), other inhibitors of receptor-ligand pairs or Fas ligand may inhibit rejection, e.g., by inducing tolerance to the transplanted xenograft. Also, rejection may be prevented or inhibited by enhancing expression of protective genes to suppress pro-inflammatory medications associated with endothelial cell activation, and to protect the donor cells, tissue or organ from apoptosis. For example, expression of the stress responsiveness gene, hemeoxygenase, (HO-1) can potentiate xenograft survival. Also, anti-apoptotic genes, e.g, which inhibit transcriptional activation can be over-expressed to enhance xenograft survival. Many genes which inhibit apoptosis have been cloned and sequenced.

Still further, endogenous porcine retroviruses may be eliminated to prevent the risk of such sequences inserting into the host genome.

Also, because complement activation is a critical mediator of hyper-acute rejection, this pathway may be inhibited by genetic modification. Specifically, the complement cascade is known to be closely regulated by a group of endothelial proteins including Decay Accelerating Factor (DAF, CD55), Membrane Cofactor Protein (MCP, CD46), and CD59, which ordinarily act as inhibitors at various points in the complement cascade. These proteins have restricted activity, i.e., they only act on homologous (same species) target molecules. Therefore, it may be beneficial to introduce genes that encode human complement-inhibiting proteins (e.g., DAF, MCP) on the vascular endothelium of porcine tissues. Also, it may be advantageous to combine these genetic approaches in order to obtain optimal results, i.e., to produce cells, tissues or organs having very low capability to elicit a rejection response.

Still further, the cells, tissues or organs may be cultured in vitro in the presence of donor cells and other agents, e.g., CTLA-41 g, immunotoxins, anti-CD40-L, prior to implantation into recipients in order to induce tolerance prior to implantation.

Of course, it may still be necessary to administer anti-rejection agents after transplantation, which include by way of example cyclosporine, glucocorticoids, FK-506, rapamycin, imuran, and derivatives thereof.

Also provided by the present invention are pigs obtained according to the above method, and offspring of those pigs.

In another aspect, the present invention provides a method for producing pig CICM (pluripotent) cells. The method comprises:

(i) inserting a desired differentiated pig cell or cell nucleus into a pig oocyte or blastomere, optionally enucleated, under conditions suitable for the formation of a nuclear transfer (NT) unit;

(ii) optionally removing the endogenous nucleus of the oocyte or blastomere if not previously enucleated;

(iii) activating the resultant nuclear transfer unit; and (iv) culturing cells obtained from said cultured NT unit to obtain pig CICM cells.

Optionally, the activated nuclear transfer unit is cultured until greater than the 2-cell developmental stage. The resultant pig CICM cells are advantageously used in the area of cell, tissue and organ transplantation.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

The present invention provides improved procedures for cloning pigs by nuclear transfer or nuclear transplantation. In the subject application, nuclear transfer or nuclear transplantation or NT are used interchangeably.

According to the invention, cell nuclei derived from differentiated pig cells are transplanted into enucleated pig oocytes or blastomeres. The nuclei are reprogrammed to direct the development of cloned embryos, which can then be transferred into recipient females to produce fetuses and offspring, or used to produce CICM cells. The cloned embryos can also be combined with fertilized embryos to produce chimeric embryos, fetuses and/or offspring.

Prior art methods have used embryonic cell types in cloning procedures. This includes work by Campbell et al. (*Nature,* 380:64-68, 1996) and Stice et al. (*Biol. Reprod.,* 54:100-110, 1996). In both of those studies, embryonic cell lines were derived from embryos of less than 10 days of gestation. In both studies, the cells were maintained on a feeder layer to prevent overt differentiation of the donor cell to be used in the cloning procedure. The present invention uses differentiated cells.

Adult cells and fetal fibroblast cells from a sheep have purportedly been used to produce sheep offspring (Wilmut et al., 1997). Studies have shown, however, that the cloning of pigs is more difficult than cloning sheep. In fact, of the mammalian species studied, cloning of sheep appears to be the easiest, and pig cloning appears to be the most difficult. Therefore, the successful cloning of pigs using differentiated cell types, preferably actively dividing non-quiescent cells, i.e., in the $G_1$, $G_2$ or M cell phase, according to the present invention is an unexpected outcome.

Thus, according to the present invention, multiplication of superior genotypes of pigs is possible. This will allow the multiplication of adult pigs with proven genetic superiority or other desirable traits. Genetic progress will be accelerated in the pig. By the present invention, potentially billions of fetal or adult pig cells can be harvested and used for the cloning procedure. This will result in many identical offspring in a short period.

The present invention also allows simplification of transgenic procedures by working with a cell source that can be clonally propagated. This eliminates the need to maintain the cells in an undifferentiated state. Thus, genetic modifications, both random integration and gene targeting, are more easily accomplished. Also by combining nuclear transfer with the ability to modify and select for these cells in vitro, this procedure is more efficient than previous transgenic embryo techniques. According to the present invention, these cells can be clonally propagated without cytokines, conditioned media and/or feeder layers, further simplifying and facilitating the transgenic procedure. When transfected cells are used in cloning procedures according to the invention, transgenic pig embryos are produced which can develop into fetuses and offspring. Also, these transgenic cloned embryos can be used to produce CICM cell lines or other embryonic cell lines. Therefore, the present invention eliminates the need to derive and maintain in vitro an undifferentiated cell line that is conducive to genetic engineering techniques.

In a preferred embodiment, which is particularly applicable for complex genetic modifications, desired differentiated cells will be genetically modified, preferably in tissue culture, these genetically modified cells used to produce a cloned fetus or animal, and differentiated cells are then derived from the cloned fetus or animal, subjected to an additional genetic modification, and the resultant twice genetically modified cells used as a cell or nuclear donor for cloning. This process, which the inventors refer to as "recloning", is useful for producing complex genetic modifications which require substantial time. Essentially, by effecting such genetic modifications in different steps, followed by cloning, it is possible to produce the desired genetic modifications without the problem of the cells potentially becoming senescent prior to effecting all the desired genetic modifications. Theoretically, this process can be repeated as many times as necessary.

Transgenic CICM cells produced according to the invention can be maintained indefinitely in vitro, thereby providing a limitless supply of undifferentiated pluripotent cells for the later production of desired differentiated cell types. In a preferred embodiment, these CICM's will be maintained in an undifferentiated state according to the method disclosed in commonly assigned U.S. Pat. No. 5,905,042, which is incorporated by reference in its entirety herein.

The present invention can also be used to produce cloned pig fetuses, offspring or CICM cells which can be used, for example, in cell, tissue and organ transplantation. By taking a fetal or adult cell from a pig and using it in the cloning procedure a variety of cells, tissues and possibly organs can be obtained from cloned fetuses as they develop through organogenesis. Cells, tissues, and organs can be isolated from cloned offspring as well. This process can provide a source of "materials" for many medical and veterinary therapies including cell and gene therapy. If the cells are transferred back into the animal from which the cells were derived, then immunological rejection is averted. Also, because many cell types can be isolated from these clones, other methodologies such as hematopoietic chimerism can be used to avoid immunological rejection among animals of the same species as well as between species.

Thus, in one aspect, the present invention provides a method for cloning a pig. In general, the pig will be produced by a nuclear transfer process comprising the following steps:

(i) obtaining desired differentiated pig cells to be used as a source of donor nuclei or donor cells;
(ii) obtaining pig oocytes or blastomeres;
(iii) optionally enucleating said oocytes or blastomeres;
(iv) transferring the desired differentiated cell or cell nucleus into the optionally enucleated oocyte or blastomere, e.g., by fusion or injection, to form NT units;
(v) enucleating the NT unit to remove endogenous oocyte or blastomere nucleus if not previously enucleated;
(vi) activating the resultant NT unit; and
(vii) transferring said cultured NT unit to a host pig such that the NT unit develops into a fetus.

Optionally, the activated nuclear transfer unit is cultured until greater than the 2-cell developmental stage. Also, optionally the host pig will contain one or more "helper" embryos, e.g., normal pig embryos, tetraploid embryos, or parthenogenetic embryos to promote development of cloned embryos.

The present invention also includes a method of cloning a genetically engineered or transgenic pig, by which a desired DNA sequence is inserted, removed or modified in the differentiated pig cell or cell nucleus prior to insertion of the differentiated pig cell or cell nucleus into the optionally enucleated oocyte or blastomere (enucleation can be effected after insertion of donor cell or nucleus).

Also provided by the present invention are cloned pigs obtained according to the above method, and offspring of those pigs. In contrast to previous transgenic and bred pigs, these clones will comprise the identical genotype as a previously existing differentiated cell or nucleus used as the nuclear transfer donor.

In addition to the uses described above, the genetically engineered or transgenic pigs according to the invention can be used to produced a desired protein, such as a pharmacologically important protein. That desired protein can then be isolated from the milk or other fluids or tissues of the transgenic pig. Alternatively, the exogenous DNA sequence may confer an agriculturally useful trait to the transgenic pig, such as disease resistance, decreased body fat, increased lean meat product, improved feed conversion, or altered sex ratios in progeny. Also, the exogenous DNA may encode one or more DNAs that inhibit rejection of such cells in a heterologous host, e.g., human. In a particularly preferred embodiment, the pig will express one or more human genes, e.g., those encoding structural proteins such as collagens, immune proteins, hormones, enzymes, clotting factors, preferably inserted in favor of the porcine counterpart. This will facilitate later recovery of the human protein as it will eliminate the need to remove homologous porcine protein, e.g., porcine factor VIII, if human factor VIII is expressed therein.

The present invention further provides for the use of NT fetuses and NT and chimeric offspring in the area of cell, tissue and organ transplantation.

In another aspect, the present invention provides a method for producing pig CICM cells. The method comprises:

(i) inserting a desired differentiated pig cell or cell nucleus into an optionally enucleated pig oocyte or blastomere, under conditions suitable for the formation of a nuclear transfer (NT) unit;
(ii) removing endogenous oocyte or blastomere nucleus if not previously enucleated;
(iii) activating the resultant nuclear transfer unit; and
(iv) culturing cells obtained from said cultured NT unit to obtain pig CICM cells.

As noted above, a preferred culturing procedure is disclosed in U.S. Pat. No. 5,905,042, incorporated by reference in its entirety herein. Optionally, the activated nuclear transfer unit is cultured until greater than the 2-cell developmental stage.

The pig CICM cells are advantageously used in the area of cell, tissue and organ transplantation, or in the production of fetuses or offspring, including transgenic fetuses or offspring.

As used herein, a fetus is the unborn young of a viviparous animal after it has taken form in the uterus. In pigs, the fetal stage occurs from 30 days after conception until birth. A mammal is an adult from birth until death.

Optionally, the NT units will be cultured to a size of at least 2 to 400 cells, preferably 4 to 128 cells, and most preferably to a size of at least about 50 cells.

Nuclear transfer techniques or nuclear transplantation techniques are known in the literature and are described in many of the references cited in the Background of the Invention. See, in particular, Campbell et al, *Theriogenology*, 43:181 (1995); Collas et al., *Mol. Report. Dev.*, 38:264-267 (1994); Keefer et al., *Biol. Reprod.*, 50:935-939 (1994); Sims et al., *Proc. Natl. Acad. Sci., USA*, 90:6143-6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation.

Differentiated refers to cells having a different character or function from the surrounding structures or from the cell of origin. Differentiated pig cells are those cells which are past the early embryonic stage. More particularly, the differentiated cells are those from at least past the embryonic disc stage (day 10 of bovine embryogenesis). The differentiated cells may be derived from ectoderm, mesoderm or endoderm.

In a preferred embodiment, the differentiated cell will be an active proliferating (non-quiescent) cell, i.e., in $G_1$, $G_2$ or M cell phase. Such cells may be obtained directly from an adult or fetal porcine, or may be isolated from an in vitro culture. Still further, such differentiating cells may be derived from a non-porcine animal, e.g., a SCID mouse, e.g., implanted with porcine immune cells. Suitable differentiated cells useful as the donor cell or nuclei include somatic and germ cells, and nuclei derived therefrom.

Pig cells may be obtained by well known methods. Pig cells useful in the present invention include, by way of example, epithelial cells, cumulus cells, neural cells, epidermal cells, keratinocytes, hematopoietic cells, melanocytes, chondrocytes, lymphocytes (B and T lymphocytes), erythrocytes, dendritic cells, macrophages, monocytes, mononuclear cells, and other immune cells, fibroblasts, cardiac muscle cells, and other muscle cells, etc. Moreover, the pig cells used for nuclear transfer may be obtained from different organs, e.g., skin, lung, pancreas, liver, stomach, intestine, heart, reproductive organs, bladder, kidney, urethra and other urinary organs, etc. Also, stem cells for specific differentiated cell types may be useful donor cells, e.g., hematopoietic stem cells. These are just examples of suitable donor cells. Suitable donor cells, i.e., cells useful in the subject invention, may be obtained from any cell or organ of the body. As noted, donor cells are intended to include both somatic and germ cells.

For example, in the case of germ cells this will include in particular primordial germ cells.

Fibroblast cells are an ideal cell type because they can be obtained from developing fetuses and adult pigs in large quantities. Fibroblast cells are differentiated somewhat and, thus, were previously considered a poor cell type to use in cloning procedures. Importantly, these cells can be easily propagated in vitro with a rapid doubling time and can be clonally propagated for use in gene targeting procedures. Again the present invention is novel because differentiated cell types are used. The present invention is advantageous because these cells can be easily propagated, genetically modified and selected in vitro.

Methods for isolation of oocytes are well known in the art. Essentially, this will comprise isolating oocytes from the ovaries or reproductive tract of a pig. A readily available source of pig oocytes is slaughterhouse materials.

For the successful use of techniques such as genetic engineering, nuclear transfer and cloning, oocytes can be matured in vitro before these cells are used as recipient cells for nuclear transfer. This process generally requires collecting immature (prophase I) oocytes from pig ovaries, e.g., pig ovaries obtained at a slaughterhouse, and maturing the oocytes in a maturation medium prior to fertilization or enucleation until the oocyte attains the metaphase II stage, which in the case of pig oocytes generally occurs about 35-45 hours post-aspiration. For purposes of the present invention, this period of time is known as the "maturation period." As used herein for calculation of time periods, "aspiration" refers to aspiration of the immature oocyte from ovarian follicles. A current preferred protocol for aspiration of porcine ovarian follicles is disclosed in the Examples which follow.

Additionally, metaphase II stage oocytes, which have been matured in vivo have been successfully used in nuclear transfer techniques. For example, mature metaphase II oocytes have been collected surgically from either non-superovulated or superovulated cows or heifers 35 to 48 hours past the onset of estrus or past the injection of human chorionic gonadotropin (hCG) or similar hormone. Similar procedures can be used in pigs. A suitable procedure is described in the Examples which follow.

The stage of maturation of the oocyte at enucleation and nuclear transfer has been reported to be significant to the success of NT methods. (See e.g., Prather et al., *Differentiation*, 48, 1-8, 1991). However, it is anticipated that non-mature oocytes can also be fused with differentiated cells or nucleus and used to produce nuclear transfer embryos. For example, the oocyte may be matured in vitro after fusion. However, in general, successful mammalian embryo cloning practices use the metaphase II stage oocyte as the recipient oocyte because at this stage it is believed that the oocyte can be or is sufficiently "activated" to treat the introduced nucleus as it does a fertilizing sperm. In domestic animals, the oocyte activation period generally ranges from about 16-52 hours, preferably about 35-45 hours post-aspiration.

For example, immature oocytes can be matured in vitro in suitable maturation medium. Preferably, but not necessarily, the porcine oocytes are matured in vitro, e.g., by placing such oocytes for about 22 hours in NCSU 37 medium (substituents identified infra), supplemented with pFF, β-mercaptoethanol, cysteine, EGF (epidermal growth factor), HCG/PMSG and cAMP, which are then washed with HECM/HEPES and sucrose, preferably three times, and then placed for about 20 hours in same NCSU 37 medium, except that the hormones are eliminated. This is preferably effected in a four well nunc plate.

Matured oocytes, wherein maturation may be effected in vitro (e.g., as described above) or in vivo, are also preferably processed prior to enucleation. This is effected in order to remove cumulus cells. This can preferably be effected by treatment with hyaluronidase followed by vortexing.

As noted, oocytes may be matured in vivo, followed by vortexing by inducing the formation of oocyte maturation in vivo and collecting such mature oocytes. For example, female porcines can be injected with PG600 and mature oocytes collected, typically, about 5 to 6 days later, i.e., 24 to 36 hours after estrus. This may be effected by removal of uterine traits from animals sent to slaughter, from which the oviduct is then dissected, preferably flushed with suitable media, and the oocytes then stripped of cumulus cells. This will be effected by the same methods as for in vitro matured oocytes, e.g., by treatment with hyaluronidase followed by vortexing.

After maturation, which if effected in vitro typically takes about 30 to 50 hours, and preferably about 40 hours, the oocytes are preferably then enucleated. However, this is not necessary as enucleation can alternatively be effected after transplantation of the donor cell or nucleus. The stripped oocytes produced by the above-described or alternative procedures are preferably screened for polar bodies, and the selected metaphase II oocytes, as determined by the presence of polar bodies, are preferably used for nuclear transfer. Enucleation may be effected before or after introduction of donor the differentiated cell or nucleus. Enucleation may be effected by known methods, such as described in U.S. Pat. No. 4,994,384, which is incorporated by reference herein. In a preferred embodiment, oocytes will be exposed to NCSU 23 medium (containing 0.2567 mg/10 ml of sucrose) and HXT for 20 minutes or longer. Enucleation is then conducted preferably in HECM/HEPES and sucrose (0.2567 mg/10 ml) media, also containing cytochalasin B. After enucleation, the oocytes are placed in a suitable medium, e.g., NCSU 23 containing sucrose (0.2567 mg/10 ml). Alternatively, metaphase II oocytes can be placed in HECM, optionally containing 7.5 micrograms per milliliter cytochalasin B (CB) and 0.15 M sucrose, for immediate enucleation. Optionally, these oocytes may be maintained in a suitable medium, for example an embryo culture medium such as NCSU 23 (see Table in the Examples) at 39° C. and 5% $CO_2$, and then enucleated later, preferably not more than 24 hours later.

Enucleation may be accomplished microsurgically using a micropipette to remove the polar body and the adjacent cytoplasm. The oocytes are screened to identify those of which have been successfully enucleated. This screening is preferably effected by staining the oocytes with a suitable dye, e.g., 1 microgram per milliliter 33342 Hoechst dye, for 20 minutes in a suitable medium, e.g., NCSU 23, and then determining visually whether enucleation has been accomplished, e.g., by viewing the oocytes under ultraviolet irradiation for less than 10 seconds. The oocytes that have been successfully enucleated can then be placed in a suitable culture medium, e.g., NCSU 23 and sucrose (0.2567 mg/10 ml), HECM and 0.15 M sucrose.

In the present invention, the recipient oocytes will preferably be enucleated at a time ranging from about 30 hours to about 50 hours after the initiation of maturation, more preferably from about 38 hours to about 46 hours after initiation of maturation, and most preferably about 42 hours after initiation of maturation.

A single porcine differentiated cell, e.g., a somatic or germ cell, pig cell or nucleus will then be transferred into the perivitelline space of a preferably enucleated oocyte or blastomere used to produce the NT unit. However, as has been noted, enucleation can be effected after fusion if so desired. The pig cell and the enucleated oocyte will be used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al., (incorporated by reference in its entirety herein) for a further discussion of this process. A variety of electrofusion media can be used including e.g., sucrose, mannitol, sorbitol and phosphate buffered solution. Fusion can also be accomplished using Sendai virus as a fusogenic agent (Graham, *Wister Inot. Symp. Monogr.*, 9, 19, 1969). A preferred fusion medium used in the Examples which follow comprises 0.28 M mannitol, 10 μM $CaCl_2$, 100 μM $MgSO_4$ and 10 mM histidine, pH 7.0.

In some cases (e.g. with small donor nuclei) it may be preferable to inject the nucleus directly into the oocyte rather than using electroporation fusion. Such techniques are disclosed in Collas and Barnes, *Mol. Reprod. Dev.*, 38:264-267 (1994), incorporated by reference in its entirety herein.

Alternatively, prior to introduction into the fusion chamber, the NT units can be gradually exposed to the fusion medium via 3 incubations containing HECM to fusion medium in ratios of 2:1, 1:2 and 0:1. The pig cell and oocyte can be electrofused by various methods, e.g., by treatment in a 500 μm chamber by application of an electrical pulse of 90-120V for about 30 μsec, about 44 hours after initiation of oocyte maturation. After fusion, the resultant fused NT units are maintained in fusion medium for 5 min, then placed in HECM for 10 min, and then in NCSU 23 plus 7.5 mg/ml CB until activation. Typically activation will be effected shortly thereafter, typically less than 24 hours later, and preferably about 1-9 hours later, and most preferably about 2 hours later.

Currently, a preferred protocol is to transfer optionally enucleated oocytes which have been treated with pronase, preferably about 400 μl/1 well, and then diluted in suitable media, e.g., HECM/HEPES, and then centrifuged, preferably at about 6 kRPM for four minutes, and then resuspended in suitable media, e.g., HECM/HEPES. Alternatively, the oocytes can be treated with TE using the same dissociation conditions as above.

In the current preferred protocol, transfer of the donor nucleus or cell is effected in a suitable medium, e.g., HECM/HEPES+sucrose (0.2567 mg/10 ml). After transfer is complete, the resultant NT embryos are then transferred to a suitable medium, e.g., NCSU 23 containing sucrose (0.2567 mg/10 ml). The NT embryos are then fused, preferably by applying 110V current for about thirty μ seconds in a suitable fusion media. As noted, the current preferred fusion medium comprises 500 ml of Sigma water, 0.28 mannitol (25.51 g), 100 μM $MgSO_4$ (0.0123 g), and 100 mM Histidine (0.776 g). However, other known fusion media can be substituted therefor. Preferably, the fused NT units will then be placed in a suitable medium, e.g., HECM/HEPES and then placed in NCSU 23 and cytochalasin B (3 μl/2 ml) for about two hours prior to activation.

Optionally one or more caspase inhibitors may be used during maturation, manipulation (stripping of cumulus cells) and/or activation to enhance blastocyst development and the production of live offspring. Examples thereof include caspase 3, caspase 8, and caspase 9.

The NT unit may be activated by known methods. Activation may be effected before, simultaneous, or after. Such methods include, e.g., culturing the NT unit at sub-physiological temperature, in essence by applying a cold, or actually cool temperature shock to the NT unit. This may be most conveniently done by culturing the NT unit at room temperature, which is cold relative to the physiological temperature conditions to which embryos are normally exposed.

Suitable activation protocols include the following:

1. Activation by Ionomycin and DMAP

1—Place oocytes in Ionomycin (5 μM) with 2 mM of DMAP for 4 minutes;

2—Move the oocytes into culture media with 2 mM of DMAP for 4 hours;

3—Rinse four times and place in culture.

2. Activation by Ionomycin DMAP and Roscovitin

1—Place oocytes in Ionomycin (5 μM) with 2 mM of DMAP for four minutes;

2—Move the oocytes into culture media with 2 mM of DMAP and 200 microM of Roscovitin for three hours;

3—Rinse four times and place in culture.

3. Activation by Exposure to Ionomycin Followed by Cytochalasin and Cycloheximide.
  1—Place oocytes in Ionomycin (5 microM) for four minutes;
  2—Move oocytes to culture media containing 5 μg/ml of cytochalasin B and 5 μg/ml of cycloheximide for five hours;
  3—Rinse four times and place in culture.
4. Activation by Electrical Pulses
  1—Place eggs in mannitol media containing 100 μM $CaCL_2$;
  2—Deliver three pulses of 1.0 $kVcm^{-1}$ for 20 μsec, each pulse 22 minutes apart;
  3—Move oocytes to culture media containing 5 μg/ml of cytochalasin B for three hours.
5. Activation by Exposure with Ethanol Followed by Cytochalasin and Cycloheximide
  2—Place oocytes in 7% ethanol for one minute;
  3—Move oocytes to culture media containing 5 μg/ml of cytochalasin B and 5 μg/ml of cycloheximide for five hours;
  4—Rinse four times and place in culture.
6. Activation by Microinjection of Adenophostin
  1—Inject oocytes with 10 to 12 picoliters of a solution containing 10 μM of adenophostin;
  2—Put oocytes in culture.
7. Activation by microinjection of sperm factor
  1—Inject oocytes with 10 to 12 picoliters of sperm factor isolated either from primates, pigs, bovine, sheep, goats, horses, mice, rats, rabbits or hamsters;
  2—Put eggs in culture.
8. Activation by microinjection of recombinant sperm factor.
9. Alternative DMAP/Ionomycin Protocol
  Place oocytes or NT units, typically about 22 to 28 hours post maturation in about 2 mM DMAP for about one hour, followed by incubation for about two to twelve hours, preferably about eight hours, in 5 μg/ml of cytochalasin B and 20 μg/ml cycloheximide.

A current preferred method for effecting activation is in HECM/HEPES (H/H) medium containing 1 mg/ml BSA, by a three step activation protocol. In the first step, the NT fusions are placed in said H/H BSA medium also containing 10 μm ionomycin (4 μl/2 ml) for about four minutes, followed by rinsing in said H/H medium, and then placing the NT fusions in NCSU 23 medium containing DMAP (1 μl/ml) for about thirty minutes. In the second step, the NT fusions are again placed in H/H medium containing 1 mg/ml BSA and also containing 5 μM ionomycin for about four minutes, followed by rinsing in H/H, and placing the rinsed oocytes in NCSU 23 and DMAP (1 μl/ml) for about thirty minutes. In the third step, the NT fusions are again placed in H/H containing 1 mg/ml BSA and further comprising 5 μM ionomycin and DMAP (1 μl/ml) for two hours. After such activation protocol, the activated NT units are then preferably transferred to a suitable medium, e.g., NCSU 23 medium. This medium, or other suitable medium, is changed as necessary, typically about the third day. On day five, about 5% FBS is preferably added and the NT units cultured to enable blastocyst formation. However, as discussed above, the NT embryos can be transferred essentially immediately after production, i.e., there may be successfully transferred at day one, while in the one cell stage.

Alternatively, the pig NT units can be activated in a 500 μm chamber by application of an electrical pulse of 30V for 30 μsec in an activation medium containing 0.28 M mannitol, 100 μM $CaCl_2$, 100 μM $MgSO_4$ and 10 mM histidine, pH 7.0. One hour later a second pulse of 15V is applied for 30 μsec. Between pulses the NT units are maintained in NCSU 23 with CB at 39° C. and 5% $CO_2$.

Still alternatively, activation may be achieved by application of known activation agents. For example, penetration of oocytes by sperm during fertilization or the activation factor contained in sperm cells can activated NT units. Also, treatments such as electrical or chemical shock, calcium ionophores, and protein kinase inhibitors may be used to activate NT embryos after fusion.

Yet alternatively, chemical activation can be effected about one to two hours after fusion by placing NT units in HECM/HEPES containing 5 μM ionomycin for four minutes, followed by washing three times in HECM/HEPES, and then placing in HECM/HEPES plus cytochalasin B of ionomycin for about four minutes, washed three times in HECM/HEPES and then placed in NCSU 23 containing 2 mM of DMAP (6-dimethylaminopurine) for about three hours. Afterward, the NT units are preferably washed about three to four times in HECM/HEPES and then placed in NCSU 23 prior to embryo transfer.

Further alternatively, after activation the NT units can be cultured for 3 to 4 hours in NCSU 23 plus CB, and thereafter in NCSU 23 without CB. As noted, the NT units can be transferred into the recipient female anytime after activation.

Alternatively, the activated NT units may then be cultured in a suitable in vitro culture medium to produce CICM cells and cell colonies. Culture media suitable for culturing and maturation of embryos are well known in the art. Examples of known media include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb, pig, or steer serum. A preferred maintenance medium includes TCM-199 with Earl salts, 10% fetal calf serum, 0.2 mM Na pyruvate and 50 μg/ml gentamycin sulphate. More preferably, the medium used is NCSU 23, and 2 to 5 days after activation the NT units are cultured in fresh NCSU 23 and 5 to 10% fetal calf serum. Any of the above may also involve co-culture with a variety of cell types such as granulosa cells, oviduct cells, BRL cells, uterine cells, and STO cells.

Another maintenance medium is described in U.S. Pat. No. 5,096,822, to Rosenkrans, Jr. et al., which is incorporated herein by reference. This embryo medium, named CR1, contains the nutritional substances necessary to support an embryo. The NT units can be cultured in NCSU 23 plus 5 to 10% FCS until the NT units reach a desired size, whereupon they are transferred to a recipient female, or are used to produce CICM cells or cell colonies. For example, these NT units can be cultured until at least about 2 to 400 cells, more preferably about 4 to 128 cells, and most preferably at least about 50 cells. Alternatively, NT embryos which are 1 cell can be introduced into recipient females, i.e., those produced on the first day of activation. The culturing will be effected under suitable conditions, i.e., about 38.5° C. and 5% $CO_2$, with the culture medium changed in order to optimize growth typically about every 2-5 days, preferably about every 3 days.

The methods for embryo transfer and recipient animal management in the present invention can be effected using standard procedures used in the embryo transfer industry.

Synchronous transfers are desirable, i.e., the stage of the NT embryo is in synchrony with the estrus cycle of the recipient female. This advantage and how to maintain recipients are discussed in Wall et al ("Development of porcine ova that were centrifuged to permit visualization of pronuclei and nuclei," *Biol. Reprod.*, 32:645-651 (1985)), the contents of which are hereby incorporated by reference.

As discussed previously, it is desirable but not necessary that the recipient female also comprise "helper" embryos. Such helper embryos include normal porcine embryos, e.g., produced by natural or artificial methods, parthenogenetic embryos (activated, non-fertilized embryos which will not give rise to live offspring), and tetraploid embryos. This has been found to enhance the development and maintenance of cloned porcines.

The number of such helper embryos can vary significantly, i.e., from about one to two to as many as one hundred. It is hypothesized that these helper embryos may produce materials, e.g., hormones and growth factors, that enhance embryonic development and/or implantation of cloned embryos. An advantage of parthenogenetic helper embryo or tetraploid helper embryo is that the only offspring which will develop into viable offspring will be the clones. However, the production of cloned offspring can be confirmed by genetic analysis, e.g., by PCR or by detecting expression or presence of cloned DNA sequence, e.g., by in situ hybridization, or by detecting expression of cloned DNA, e.g., by use of radiolabeled antibody or other probe.

As noted, the present invention is particularly useful for producing cloned genetically engineered or transgenic pigs. The present invention is advantageous in that transgenic procedures can be simplified by working with a differentiated cell source that can be clonally propagated. In particular, the differentiated cells used for donor nuclei have a desired DNA sequence inserted, removed or modified. Those genetically altered, differentiated cells are then used for nuclear transplantation with enucleated oocytes.

Any known method for inserting, deleting or modifying a desired DNA sequence from a mammalian cell may be used for altering the differentiated cell to be used as the nuclear donor. These procedures may remove all or part of a DNA sequence, and the DNA sequence may be heterologous. Included is the technique of homologous recombination, which allows the insertion, deletion or modification of a DNA sequence or sequences at a specific site or sites in the cell genome. In a preferred embodiment, endogenous porcine genes will be "knocked out" and the human homolog, e.g., a DNA encoding an immunological protein, hormone, structural protein, clotting factor, enzyme, receptor, or other cloned gene, knocked in.

The present invention can thus be used to provide adult pigs with desired genotypes. Multiplication of adult pigs with proven genetic superiority or other desirable traits is particularly useful, including transgenic or genetically engineered animals, and chimeric animals. Thus, the present invention will allow production of single sex offspring, and production of pigs having improved meat production, reproductive traits and disease resistance. Furthermore, cell and tissues from the NT fetus, including transgenic and/or chimeric fetuses, can be used in cell, tissue and organ transplantation for the treatment of numerous diseases as described below in connection with the use of 5 CICM cells. Hence, transgenic pigs have uses including models for diseases, xenotransplantation of cells and organs, and production of pharmaceutical proteins.

As discussed, in a preferred embodiment, endogenous structural genes, e.g., collagens, will be replaced by human collagen genes. In another preferred embodiment, porcine serum albumin gene will be replaced by HSA gene.

For production of CICM cells and cell lines, after NT units of the desired size are obtained, the cells are mechanically removed from the zone and are then used. This is preferably effected by taking the clump of cells which comprise the NT unit, which typically will contain at least about 50 cells, washing such cells, and plating the cells onto a feeder layer, e.g., irradiated fibroblast cells. Typically, the cells used to obtain the stem cells or cell colonies will be obtained from the inner most portion of the cultured NT unit which is preferably at least 50 cells in size. However, NT units of smaller or greater cell numbers as well as cells from other portions of the NT unit may also be used to obtain ES cells and cell colonies. The cells are maintained in the feeder layer in a suitable growth medium, e.g., alpha MEM supplemented with 10% FCS and 0.1 mM β-mercaptoethanol (Sigma) and L-glutamine. The growth medium is changed as often as necessary to optimize growth, e.g., about every 2-3 days.

This culturing process results in the formation of CICM cells or cell lines. One skilled in the art can vary the culturing conditions as desired to optimize growth of the particular CICM cells. Also, genetically engineered or transgenic pig CICM cells may be produced according to the present invention. That is, the methods described above can be used to produce NT units in which a desired DNA sequence or sequences have been introduced, or from which all or part of an endogenous DNA sequence or sequences have been removed or modified. Those genetically engineered or transgenic NT units can then be used to produce genetically engineered or transgenic CICM cells. As noted previously, a preferred means for maintaining such CICM's in culture in an undifferentiated state is discussed in U.S. Pat. No. 5,905,042, incorporated by reference herein.

The resultant CICM cells and cell lines have numerous therapeutic and diagnostic applications. Most especially, such CICM cells may be used for cell transplantation therapies.

In this regard, it is known that mouse embryonic stem (ES) cells are capable of differentiating into almost any cell type, e.g., hematopoietic stem cells. Therefore, pig CICM cells produced according to the invention should possess similar differentiation capacity. The CICM cells according to the invention will be induced to differentiate to obtain the desired cell types according to known methods. For example, the subject pig CICM cells may be induced to differentiate into hematopoietic stem cells, neural cells, muscle cells, cardiac muscle cells, liver cells, cartilage cells, epithelial cells, urinary tract cells, neural cells, etc., by culturing such cells in differentiation medium and under conditions which provide for cell differentiation. Medium and methods which result in the differentiation of CICM cells are known in the art as are suitable culturing conditions.

For example, Palacios et al., *Proc. Natl. Acad. Sci., USA*, 92:7530-7537 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen, *J. Reprod. Fertil. Dev.*, 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, *Dev. Biol.*, 168:342-357 (1995) teaches in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein.

Thus, using known methods and culture medium, one skilled in the art may culture the subject CICM cells, including genetically engineered or transgenic CICM cells, to obtain desired differentiated cell types, e.g., neural cells, muscle cells, hematopoietic cells, etc. It has been demonstrated by the successful production of chimeric animals (pigs and bovines) that the culturing method disclosed in U.S. Pat. No. 5,905,042, gives rise to pluripotent CICMs.

The subject CICM cells may be used to obtain any desired differentiated cell type. Therapeutic usages of such differentiated cells are unparalleled. For example, hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, obtaining CICM cells as described above, and culturing such cells under conditions which favor differentiation, until hematopoietic stem cells are obtained. Such hematopoietic cells may be used in the treatment of diseases including cancer and AIDS.

The present invention can be used to replace defective genes, e.g., defective immune system genes, or to introduce genes which result in the expression of therapeutically beneficial proteins such as growth factors, lymphokines, cytokines, clotting factors, receptors, enzymes, etc.

DNA sequences which may be introduced into the subject CICM cells include, by way of example, those which encode epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokines (interleukins, interferons, colony stimulating factors, tumor necrosis factors (alpha and beta), etc.), therapeutic enzymes, etc.

The present invention includes the use of pig cells in the treatment of human diseases. Thus, pig CICM cells, NT fetuses and NT and chimeric offspring (transgenic or non-transgenic) may be used in the treatment of human disease conditions where cell, tissue or organ transplantation is warranted. In general, CICM cell, fetuses and offspring according to the present invention can be used within the same species (autologous, syngenic or allografts) or across species (xenografts). For example, brain cells from pig NT fetuses may be used to treat Parkinson's disease.

Also, the subject CICM cells, may be used as an in vitro model of differentiation, in particular for the study of genes which are involved in the regulation of early development. Also, differentiated cell tissues and organs using the subject CICM cells may be used in drug studies.

Further, the subject CICM cells may be used as nuclear donors for the production of other CICM cells and cell colonies.

In order to more clearly describe the subject invention, the following examples are provided.

EXAMPLES

Materials and Methods for Pig Cloning

Modified NCSU 37 Medium (mNCSU 37)

| Component | Mol. Wt. | Conc. (mM) | g/l |
|---|---|---|---|
| NaCl | 58.45 | 108.73 | 6.3553 |
| NaHCO$_3$ | 84.00 | 25.07 | 2.1059 |
| KCl | 74.55 | 4.78 | 0.3563 |
| KH$_2$PO$_4$ | 136.09 | 1.19 | 0.1619 |
| MgSO$_4$7H$_2$O | 246.50 | 1.19 | 0.2933 |
| CaCl$_2$2H$_2$O | 147.00 | 1.70 | 0.2499 |
| Glucose | 180.20 | 5.55 | 1.0000 |
| Glutamine | 146.10 | 1.00 | 0.1461 |
| Sorbitol | 182.20 | 12.00 | 2.1864 |
| Insulin | — | 5 mg/l | 0.0050 |
| Penicillin G | — | 100 IU/l | 0.0650 |
| Streptomycin | — | 50 mg/l | 0.0500 |

Use 18 mohm, RO, DI water.
pH should be 7.4, Check osmolarity and record.
Sterilize by vacuum filtration (0.22 μm), date and initial bottle.
Store at 4° C. and use within 10 days.

Modified TL-Hepes-PVA Medium (Hepes-PVA)

| Component | Mol. Wt. | Conc. (mM) | g/l |
|---|---|---|---|
| NaCl | 58.45 | 114.00 | 6.6633 |
| KCl | 74.55 | 3.20 | 0.2386 |
| NaHCO$_3$ | 84.00 | 2.00 | 0.1680 |
| NaH$_2$PO$_4$ | 120.00 | 0.34 | 0.0408 |
| Na Lactate** | 112.10 | 10.00 | 1.868 ml |
| MgCl$_2$6H$_2$O | 203.30 | 0.50 | 0.1017 |
| CaCl$_2$2H$_2$O* | 147.00 | 2.00 | 0.2940 |
| Sorbitol | 182.20 | 12.00 | 2.1864 |
| HEPES | 238.30 | 10.00 | 2.3830 |
| Na Pyruvate | 110.00 | 0.20 | 0.0220 |
| Gentamycin | — | — | 500 μl |
| Penicillin G | — | — | 0.0650 |
| PVA | 10,000 | — | 0.1000 |

**60% syrup
*Add CaCl$_2$2H$_2$O last, slowly to prevent precipitation
Use 18 mohm, RO, DI water.
Adjust pH to 7.4, Check osmolarity and record.
Sterilize by vacuum filtration (0.22 μm), date and initial bottle.
Store at 4° C. and use within 10 days.

NCSU 23 Medium

| Component | Mol. Wt. | Conc. (mM) | g/l |
|---|---|---|---|
| NaCl | 58.45 | 108.73 | 6.3553 |
| NaHCO$_3$ | 84.00 | 25.07 | 2.1059 |
| KCl | 74.55 | 4.78 | 0.3563 |
| KH$_2$PO$_4$ | 136.09 | 1.19 | 0.1619 |
| MgSO$_4$7H$_2$O | 246.50 | 1.19 | 0.2933 |
| CaCl$_2$2H$_2$O | 147.00 | 1.70 | 0.2499 |
| Glucose | 180.20 | 5.55 | 1.0000 |
| Glutamine | 146.10 | 1.00 | 0.1461 |
| Taurine | 125.10 | 7.00 | 0.8757 |
| Hypotaurine | 109.10 | 5.00 | 0.5455 |
| BSA | — | 0.4% | 4.0000 |

-continued

| Component | Mol. Wt. | Conc. (mM) | g/l |
|---|---|---|---|
| Penicillin G | — | 100 IU/l | 0.0650 |
| Streptomycin | — | 50 mg/l | 0.0500 |

Use 18 mohm, RO, DI water.
pH should be 7.4, Check osmolarity and record.
Sterilize by vacuum filtration (0.22 μm) using red Nalgene filters, date and initial bottle.
Store at 4° C. and use within 10 days.
NOTE: BSA type is important. Preferably use Sigma BSA catalog #A-7906. Also, Pen G/Strept is optional.

Maturation Medium (MAT):

18.0 ml mNCSU 37

2.0 ml porcine follicular fluid (pFF)

7.0 μl of diluted β-Mercaptoethanol (dilute 10 μl β-Mercaptoethanol to 990 μl mNCSU 37; 50 μM final concentration)

0.002 g cysteine (0.6 mM final concentration)

20 μl EGF Stock (Epidermal Growth Factor from 10 ng/μl EGF stock)

Protocol for Aspiration of Porcine Ovarian Follicles:

Follicles are graded visually for size. Follicles that are 3 mm×3 mm up to 7 mm×7 mm are considered to be good candidates for aspiration. By contrast, follicles that are larger, especially those that are larger than 1 cm×1 cm are poor candidates for aspiration.

A 10 cc syringe with an 18 gauge needle is preferably used to draw up 1 ml of heparin (concentration of 100 IU/ml) which is then held upright and the heparin solution drawn down to the 10 cc line to coat the inside of the syringe. The heparin is then discarded from the syringe. The ovary is then held in one hand and the syringe in the other hand.

The needle is then positioned bevel down and pushed into the follicle with slight drawback on the syringe until the follicle collapses because all the follicular fluid along with the follicle have been extracted. A slight wiggling motion back and forth during the aspiration process inside the follicle has been found to promote the collapse of the follicle and removal of all the follicle contents.

Aspiration is continued to obtain as many follicles as possible until the 10 cc mark is obtained. The needle is then removed from the syringe and the follicular fluid is deposited in a collection tube.

Care should be taken to remove the needle when depositing the follicular fluid in the tube in order to avoid stripping of the cumulus cells as well as damaging the oocytes. Also, it is desirable to aspirate as many follicles of good size in a particular ovary before discarding the ovary and moving on to the next one. For optimal results, it is also desirable to change the heparin-coated syringe for each set of tracts.

Porcine Follicular Fluid Preparation

Porcine follicular fluid (pFF), typically about 3-6 mm follicles, is collected from prepubertal gilts. The oocytes and follicular cells are allowed to settle therefrom, e.g., by waiting for about 5-10 minutes. The pFF is then aspirated and removed to 15 ml conical tubes. This is then centrifuged on Sorvall at 4° C. at 3000 rpm for 30 minutes. The tubes are removed and the pFF is collected from above the pellet, pooled, and filtered through a 0.8 μm, followed by a 0.45 μm filter (Sterivex). The filtered material is then aliquoted to 1.5 ml sterile microfuge tubes and then frozen at −20° C. until use.

Epidermal Growth Factor Stock (EGF) and Preparation

100 μg EGF 10 ml mNCSU 37 with 0.1% BSA

Mix well. Aliquot to 25 μl, freeze at −20° C.

Equine Chorionic Gonadotropin and Human Chorionic Gonadotropin Stock for MAT (PMSG/hCG) and Preparation ECG (PMSG 6000; Intervet Inc., Millsboro; DE 19966)
This material is diluted from 6000 IU to 2000 IU/ml by the addition of 3 ml dH$_2$O. hCG (Chorulon; Intervet Inc.)
The hCG material is diluted from 10,000 IU to 2000 IU/ml by the addition of 5 ml dH$_2$O.
Afterward, 1 ml of diluted PMSG and 1 ml of diluted hCG are mixed to get 1000 IU/ml of each hormone. Fifty μl aliquots are then made up and frozen at −20° C. The remaining PMSG and hCG stocks are also frozen.

db-cAMP 100 mM Stock and Preparation
25 mg db-cAMP (stored in dessicator at −20° C.)
0.509 ml dH$_2$O
The above materials are well mixed and used to produce 50 μl aliquots which are then frozen at −20° C.

Activation Medium
Same as HECM/HEPES except contains 1 mg/ml BSA.

Antibiotic/Antimycotic (Ab/Am)
100 U/l Penicillin, 100 μg/l streptomycin and 0.25 μg/l amphotericin B, (Gibco #15240-062)
Ten ml aliquot of the above materials are added per liter of saline. Ten μl of this mixture is added per ml.

Oocyte-Cumulus Complex (OCC) Collection
Ovaries are transported to the lab at 25° C. and immediately washed with 0.9% saline with antibiotic/antimycotic (10 ml/L; Gibco #600-5240g). Follicles between 3-6 mm are aspirated using 18 g needles and 50 ml Falcon tubes connected to vacuum system (GEML bovine system). After a tube is filled, the OCC's are allowed to settle for 5-10 minutes. Follicular fluid (pFF) is aspirated and saved for use in culture system if needed (see pFF preparation protocol below).

Preferred Protocol for In Vivo Oocyte Recovery and Transfer of Nuclear Transfer Pig Embryos Landrance×York or Landrance×Hampshire Gilts of 225 to 275 pounds are injected with PG600 and 5 to 6 days later (24 to 36 hours after the onset of estrus) the animals are then sent to slaughter. The uterine tracts are recovered and placed in an insulated container, and taken to the laboratory.

The oviduct is dissected from the uterus and flushed with buffer media. Thereafter, oocytes are stripped from cumulus cells as described supra for the in vitro matured oocytes.

After activation, eggs are loaded into a 5½ inch Tom Cat catheter (Sovereign Cat. #8890-703021) and surgically transferred into the oviduct of a synchronous recipient gilt (same breed and 200 to 300 pounds). Half of the total number of embryos is transferred into each oviduct and typically no more than 100 NTs are transferred per animal. In some instances, 10 to 20 naturally produced two to four-cell embryos are transferred along with the NTs as "helper" embryos. Caspase inhibitors optionally may be included in the buffer media to enhance embryo development and maintenance. The gilts are anesthetized using 1 ml per 50 pounds of a mix of the 250 mg of Xylazine, 250 mg of ketamine and 500 mg of Telazol reconstituted in 5 ml. After implantation, recipient gilts are preferably moved to a new isolated facility.

Pregnancy check is preferably performed thirty days after surgery, typically by ultrasound. The fetuses can be retrieved at that time by C-section, and analyzed by PCR and Southern Blot in order to determine which one of them was produced by nuclear transfer. Alternatively, cloned fetuses will be allowed to develop to full term and be born by natural methods or C-section.

OCC Washing

OCCs are resuspended in 20 ml Hepes-PVA and allowed to settle; repeat 2 times. After last wash, OCCs are moved to grid dishes and selected for culture. Selected OCCs are washed twice in 60 mm dishes of Hepes-PVA. All aspiration and oocyte recovery are performed at room temperature (approx. 25° C.).

In Vitro Maturation (IVM)

The washed OCCs (about 50) are placed in a four-well Nunc plate tje we;;s pf which each contain 0.5 ml of Maturation medium (described above) for about 22 hours. Afterward, the oocytes are then placed in the same medium except lacking hormones for about twenty hours.

Isolation of Primary Cultures of Porcine Embryonic and Adult Fibroblast Cells

Primary cultures of porcine fibroblasts are obtained from pig fetuses 30 to 114 days post-fertilization, preferably 35 days. The head, liver, heart and alimentary tract are aseptically removed, the fetuses minced and incubated for 30 minutes at 37° C. in prewarmed trypsin EDTA solution (0.05% trypsin/0.02% EDTA; GIBCO, Grand Island, N.Y.). Fibroblast cells are plated in tissue culture dishes and cultured in fibroblast growth medium (FGM) containing: alpha-MEM medium (BioWhittaker, Walkersville, Md.) supplemented with 10% fetal calf serum (FCS) (Hyclone, Logen, Utah), penicillin (100 IU/ml) and streptomycin (50 μl/ml). The fibroblasts are grown and maintained in a humidified atmosphere with 5% $CO_2$ in air at 37° C.

Adult fibroblast cells are isolated from the lung and skin of a pig. Minced lung tissue is incubated overnight at 10° C. in trypsin EDTA solution (0.05% trypsin/0.02% EDTA; GIBCO, Grand Island, N.Y.). The following day tissue and any disassociated cells are incubated for one hour at 37° C. in prewarmed trypsin EDTA solution (0.05% trypsin/0.02% EDTA; GIBCO, Grand Island, N.Y.) and processed through three consecutive washes and trypsin incubations (one hr). Fibroblast cells are plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 μl/ml). The fibroblast cells can be isolated at virtually any time in development, ranging from approximately post embryonic disc stage through adult life of the animal (porcine day 9 to 10 after fertilization to 5 years of age or longer).

Preparation of Fibroblast Cells for Nuclear Transfer

Examples of Fetal Fibroblasts Which May be Used as Donor Nuclei are:

1. Proliferating fibroblast cells that are not synchronized in any one cell stage or serum starved or quiescent can serve as nuclear donors. The cells from the above culture are treated for 10 minutes with trypsin EDTA and are washed three times in 100% fetal calf serum. Single cell fibroblast cells are then placed in micromanipulation drops of HbT medium (Bavister et al., 1983). This is done 10 to 30 min prior to transfer of the fibroblast cells into the enucleated pig oocyte. Preferably, proliferating transgenic fibroblast cells having the CMV promoter and green fluorescent protein gene (9th passage) are used to produce NT units.

2. By a second method, fibroblast cells are synchronized in G1 or G0 of the cell cycle. The fibroblast cells are grown to confluence. Then the concentration of fetal calf serum in the FGM is cut in half over four consecutive days (day 0=10%, day 1=5%, day 2-2.5%, day 3=1.25%, day 4=0.625%. On the fifth day the cells are treated for 10 minutes with trypsin EDTA and washed three times in 100% fetal calf serum. Single cell fibroblasts are then placed in micromanipulation drops of HbT medium. This is done within 15 min prior to transfer of the fibroblast cells into the enucleated pig oocyte.

Alternatively, donor cells, e.g., fibroblasts can be obtained directly from a live animal, e.g., an adult porcine, e.g., from a tissue or fluid source.

Removal of Cumulus Cells

After a maturation period, which ranges from about 30 to 50 hours, and preferably about 42 hours, the oocytes can preferably be enucleated. Removal of cumulus cells is preferably effected prior to enucleation by contacting cells with H/H media containing 0.68 mg/ml of hyaluronidase followed by vortexing for about three minutes. Alternatively, prior to enucleation the oocytes can be removed and placed in HECM (Seshagiri and Bavister, 1989) containing 1 milligram per milliliter of hyaluronidase prior to removal of cumulus cells. This may be effected by repeated pipetting through very fine bore pipettes or by vortexing briefly (about 3 minutes). The stripped oocytes are then screened for polar bodies, and the selected metaphase II oocytes, as determined by the presence of polar bodies, are then used for nuclear transfer.

Enucleation:

A current preferred procedure comprises exposure of oocytes to NCSU 23+sucrose+HXT for at least 20 minutes, followed by enucleation effected in H/H medium containing sucrose and cytochalasin B. After enucleation, the oocytes are preferably placed in NCSU 23 containing sucrose before transfer.

Transfer:

Cells for transfer are preferably treated with pronase or TE. In the case of pronase, the cells are treated with 400 μl well, allowed to incubate and then diluted in H/H and then spun at 6 KRPM for four minutes, and then resuspended in H/H for use.

In the case of TE, the same protocol is used. Transfer is then preferably effected in H/H containing sucrose and when complete, the cells are placed in NCSU 23 containing sucrose for fusion.

Fusion Media:

| Recipe: | 500 mL of Sigma water | |
|---|---|---|
| | .28 mannitol | 25.51 g |
| | 100 μM $MgSO_4$ | .0123 g |
| | 10 mM histidine | .776 g |

Fusion:

Nuclear transfer units are preferably put through a gradient of H/H and mannitol 1:2, 1:1, and 0:2, and then fused in a 600 μm chamber, and flooded with mannitol.

The cells are electrofused, by placing cells for 30 μsec @100 V. After fusion, the NT units are placed in pure H/H and then into NCSU 23+Cyto B (3 μl/2 ml), preferably for two hours before activation.

Activation

Examples of methods of activation which may be used, typically at about 47 to 49 hours post maturation, include the following procedures, identified previously in the present application. As noted, activation may be effected prior, proximate, or after fusion.

1. Ionomycin/DMAP Procedure:

NT units are placed in H/H medium containing 1 mg/ml BSA+10 μM ionomycin (4 μl/2 ml) for four minutes, rinsed with H/H and then placed in NCSU 23+DMAP (1 μl/ml) for thirty minutes. Afterward, the NT units are placed in the same H/H medium containing BSA (1 μl/ml) BSA and 5 μM ionomycin, and treated for thirty minutes.

Afterward, the NT units are placed in the same H/H medium containing 1 mg/ml BSA+2.5 μM ionomycin and DMAP for two more hours.

The NT units are then rinsed to remove DMAP, and then cultured in NCSU 23. The media is changed on day three and 5% FBS is added late on day five, and the NT units cultured until blastocysts form.

2. Single activation pulse. NT units are removed from the NCSU 23 plus CB and washed three times in activation medium. After equilibration, the NT units are placed into the fusion chamber (500 μm gap) filled with activation medium as described in the fusion procedure. A pulse of 30 V for 30 μsec is applied. Then the NT units are immediately washed three times in HECM HEPES and cultured (39° C., 5% $CO_2$) in NCSU 23 for 2 more hours until embryo transfer or in vitro culture (39° C., 5% $CO_2$ in NCSU 23). If cultured, NT units are placed in fresh NCSU 23 plus 5% fetal calf serum on day 2 of culture. The results in Table 1 indicate that oocytes can be activated using this procedure and that they have developmental capabilities.

3. Two activation pulses. NT units are removed from the NCSU 23 plus CB and washed three times in activation medium. After equilibration the NT units are placed back into the fusion chamber (500 μm gap) filled with activation medium as described in the fusion procedure. A pulse of 30 V for 30 μsec is applied. Then the NT units are immediately washed three times in HECM HEPES, placed back in NCSU 23 plus CB, and cultured in this at 39° C., 5% $CO_2$, until the next electrical pulse 1 hr later. After 1 hr this time the activation medium equilibration step is repeated and a pulse of 15 V for 30 μsec is applied. Then the NT units are immediately washed three times in HECM HEPES, placed back in NCSU 23 plus CB, and cultured in this medium at 39° C., 5% $CO_2$, for 2 to 6 more hours. The NT units are then cultured using the same procedure described above in 1. The results in Table 1 indicate that oocytes can be activated using this procedure and that they have developmental capabilities. The same is true for nuclear transfer embryos. Four blastocyst stage NT units were produced with the two pulse activation procedure.

4. Sperm factor. First described in mammalian sperm by Stice and Robl (*Mol. Reprod. Dev.*, 25:272-280 (1990)) (the contents of which are hereby incorporated by reference), this factor causes activation in oocytes. The method of sperm factor isolation from pig sperm cells and microinjection is described in Fissore et al. (*Mol. Reprod. Dev.*, 46:176-189 (1997)), the contents of which are hereby incorporated by reference. NT units are removed from the NCSU 23 plus CB and placed in micromanipulation plates described above for enucleation and fibroblast transfer. Using a micro-injection needle (1 μm opening) filled with sperm factor the oocytes undergo activation after the delivery of the factor into the cytoplasm of the NT unit. After microinjection, the NT embryos are washed in HECM HEPES and held in NCSU 23 plus CB for 2 to 6 hours, and thereafter in NCSU 23 until embryo transfer.

TABLE 1

Development of activated oocytes and NT units using different activation procedures.

| | number given activation stimulus | number cleaved (began to develop) [%] | number to blastocyst stage (eight day old embryos) [%] |
|---|---|---|---|
| Single pulse oocytes | 52 | 6[12] | 1[2] |
| Double pulse oocytes | 85 | 8[10] | 3[4] |
| Double pulse NT units | 55 | 10[18] | 4[7] |
| Sperm-factor oocytes | 49 | 4[8] | 2[4] |

Embryo Transfer

Methods of one cell embryo transfer in pigs are well known (see, for example, Pinkert et al., 1993, the contents of which are hereby incorporated by reference). Typically, 20 to 30 NT and up to 100 NT units are synchronously transferred into the oviduct of bred or unbred gilts. After and beyond 29 days of gestation, nuclear transfer fetuses (transgenic or non-transgenic) can be recovered from the recipient gilt. Alternatively, the fetuses are allowed to go to term (114 day gestation) and cloned pig offspring are produced. As noted, such gilts will also preferably contain "helper" embryos, e.g., normal porcine embryos, parthenogenetic porcine embryos, or tetraploid embryos. The number of helper embryos may vary from 1 to about 50, typically 2 to 4.

Use of Caspase Inhibitor During In Vitro Maturation, Stripping of Oocytes or Activation As discussed above, it has been discovered that the addition of caspase inhibitors, e.g., Caspase 3, 8 or 9, enhances the number of blastocysts that arise from NT procedures. Some data in support of this discovery are provided in the Table below.

| Treatment | n | blastocyst | % blastocyst | average cell number |
|---|---|---|---|---|
| Caspases during stripping and activation | | | | |
| Control | 44 | 1 | 2 | 39 |
| Caspase 3 | 47 | 6 | 13 | 30.3 |
| Caspase 9 | 30 | 3 | 10 | 41 |
| Control | 76 | 3 | 4 | 33.6 |
| Caspase 3 | 94 | 10 | 11 | 20 |
| Caspase 8 | 283 | 5 | 2 | 14 |

-continued

| Treatment | n | blastocyst | % blastocyst | average cell number |
|---|---|---|---|---|
| Caspases during maturation | | | | |
| Control | 114 | 0 | 0 | 0 |
| Caspase 3 and 9 | 125 | 9 | 7 | 29 |

Also, for the reader's convenience, the current preferred protocol for transfer of porcine oocytes being used by the inventors is summarized below.

Summary of Preferred Cloning Methods and Materials

Protocol for Nuclear Transfer of Porcine Oocytes:

In Vitro Maturation:
 22 hours in NCSU 37+PFF+B-mercaptoethanol+cysteine+EGF+1000 IU of HCG/PMSG & cAMP during shipping, rinse with H/H three times
 20 hours in above media without hormones in a four-well nunc plate.

Processing of Porcine Oocytes:
 Stripping with 0.68 mg/ml of Hyal and vortex on three for three minutes.

Media needed:
 HECM/HEPES+sucrose (0.2567 mg/10 ml)
 NCSU 23+sucrose (0.2567 ml/10 ml)
 NCSU 23

Fusion Media:

| | 10 µM Mannitol | |
|---|---|---|
| Recipe: | 500 mL of Sigma water | |
| | .28 Mannitol | 25.51 g |
| | 100 µM MgSO$_4$ | .0123 g |
| | 10 mM Histidine | .776 k |

Fusion:
 Nuclear Transfer Units are put through a gradient of H/H and Mannitol 1:2, 1:1, and 0:2 and then fused in a 600 µm chamber, and flooded with Mannitol.
 Fusion is effected by applying 100V electricity for 30,u seconds. Fusions are immediately placed in pure H/H and then into NCSU 23+Cyto B (3 µl/2 ml) for two hours before activation.

Enucleation:
 Oocytes are exposed to NCSU 23+sucrose+HXT for at least twenty minutes.
 Enucleation is performed in H/H+ sucrose+cyto B.
 Oocytes are then put into NCSU 23+sucrose before transfer.

Transfer:
 Cells prepared with either pronase or TE
 Pronase—400 µl per well, let sit, dilute in H/H spin 6 KRPM for four minutes, resuspend in H/H for use
 TE—Same protocol for cells disassociation.
 Transfer is done in H/H+sucrose and when complete back into NCSU 23+sucrose for fusion.

Activation Media:
 H/H Z1 (same as H/H but with 1 mg/ml BSA)
 Three separate treatments separated by thirty minutes.
  1. H/H Z1+10 µM Ionomycin (4 µl/2 ml) for four minutes, rinse with H/H and then put in NCSU 23+DMAP (1 µl/ml) for thirty minutes.
  2. H/H Z1+51+2.5 µM Ionomycin and then DMAP for two more hours.
 Activated NT units are rinsed to remove DMAP and then cultured in NCSU 23.
 Media is changed at day three and 5% FBS is added late on day five, and cultured until blastocysts.

While the invention has been described with respect to certain specific embodiments, it will be appreciated that many modifications and changes thereof may be made by those skilled in the art without departing from the spirit of the invention. It is intended, therefore, by the appended claims to cover all modifications and changes that fall within the true spirit and scope of the invention.

What is claimed is:

1. A method for cloning a porcine fetus or live offspring comprising
 (i) activating a porcine oocyte that optionally is enucleated;
 (ii) transferring a non-quiescent differentiated porcine cell or nucleus from a non-quiescent differentiated porcine cell into said porcine oocyte after or simultaneous to said activating step (i) to produce a nuclear transfer unit;
 (iii) removing the endogenous oocyte nucleus if the oocyte is not previously enucleated; and
 (iv) transferring said nuclear transfer unit, after an optional culturing step, into a female porcine to produce a porcine fetus or offspring.

2. The method according to claim 1, wherein DNA is inserted, deleted, substituted, or modified in said differentiated porcine cell or porcine cell nucleus, thereby resulting in the production of a genetically altered nuclear transfer unit.

3. The method of claim 1 further comprising the use of a caspase inhibitor during maturation, stripping of cumulus cells, and/or activation.

4. The method of claim 3, wherein said caspase inhibitors consist of inhibitors of caspase-3, caspase-8, or caspase-9.

5. The method of claim 1, wherein said porcine oocyte is an enucleated oocyte.

6. The method of claim 1, wherein said nuclear transfer unit is cultured prior to transfer.

* * * * *